(12) United States Patent
Thompson et al.

(10) Patent No.: US 6,889,084 B2
(45) Date of Patent: May 3, 2005

(54) IMPLANTABLE MEDICAL DEVICE INCORPORATING MINIATURIZED CIRCUIT MODULE

(75) Inventors: David L. Thompson, Andover, MN (US); Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 66 days.

(21) Appl. No.: 10/403,742

(22) Filed: Mar. 31, 2003

(65) Prior Publication Data

US 2004/0015199 A1 Jan. 22, 2004

Related U.S. Application Data

(62) Division of application No. 09/708,307, filed on Nov. 8, 2000, now Pat. No. 6,567,703.

(51) Int. Cl.[7] .............................................. A61N 1/375

(52) U.S. Cl. ........................................... 607/36; 607/2

(58) Field of Search ............................. 607/2, 4–5, 32, 607/36–37, 60

(56) References Cited

U.S. PATENT DOCUMENTS

| | | | |
|---|---|---|---|
| 4,254,775 A | | 3/1981 | Langer ........................... 607/5 |
| 4,616,655 A | * | 10/1986 | Weinberg et al. ............... 607/2 |
| 4,681,111 A | | 7/1987 | Silvian ........................... 607/59 |
| 5,265,588 A | | 11/1993 | Nelson et al. .................. 607/5 |

(Continued)

FOREIGN PATENT DOCUMENTS

WO   WO 99/18611   *   4/1999   ........... H01L/25/16

OTHER PUBLICATIONS

Burghartz, et al., "RF Circuit design Aspects of Spiral Inductors on Silicon", *IEEE Journal of Solid–State Circuits*, vol. 33, No. 12, Dec., 1998, pp. 2028–2034.

Dec et al., "Micromachined Electro–Mechanically Tunable Capacitors and Their Applications to RF IC's", *IEEE Transactions on Microwave Theory and Techniques*, vol. 46, No. 12, Dec. 1998, pp. 2587–2595.

Hisamoto, et al., "Suspended SOI Structure for Advanced 0.1 $\mu$m CMOS RF Devices", *IEEE Transactions on Electron Devices*, vol. 45, No. 5, May 1998, pp. 1039–1045.

Kamogawa, et al, "A Novel High–Q and Wide–Frequency–Range Inductor Using Si 3–D MMIC Technology", *IEEE Microwave and Guided Wave Letters*, vol. 9, No. 1, Jan. 1999, pp. 16–18.

Larson, "Integrated Circuit Technology Options for RFIC's—Present Status and Future Directions", *IEEE Journal of Solid–State Circuits*, vol. 33, No. 3, Mar. 1998, pp. 387–399.

Niknejad, et al., "Analysis, Design, and Optimization of Spiral Inductors and Transformers for Si RF IC's", *IEEE Journal of Solid–State Circuits*, vol. 33, No. 10, Oct. 1998, pp. 1470–1481.

Ribas, et al., "Micromachined Planar Spiral Inductor in Standard GaAs HEMT MMIC Technology", *IEEE Electron Device Letters*, vol. 19, No. 8, Aug. 1998, pp. 285–287.

*Primary Examiner*—Carl Layno
(74) *Attorney, Agent, or Firm*—Girma Wolde-Michael; Daniel G. Chapik (57) ABSTRACT

Implantable medical devices (IMDs) having RF telemetry capabilities for uplink transmitting patient data and downlink recieving programming commands to and from an external programmer having an improved RF module configured to occupy small spaces within the IMD housing to further effect the miniaturization thereof. An RF module formed of an RF module substrate and at least one IC chip and discrete components has a volume and dimensions that are optimally minimized to reduce its volumetric form factor.

10 Claims, 6 Drawing Sheets

U.S. PATENT DOCUMENTS

| | | |
|---|---|---|
| 5,342,408 A | 8/1994 | deCoriolis et al. ............. 607/32 |
| 5,416,356 A | 5/1995 | Staudinger et al. .......... 257/531 |
| 5,535,097 A * | 7/1996 | Ruben et al. ................ 361/736 |
| 5,626,620 A | 5/1997 | Kieval et al. ................... 607/9 |
| 5,683,432 A | 11/1997 | Goedeke et al. ............... 607/32 |
| 5,767,791 A | 6/1998 | Stoop et al. ........... 340/870.11 |
| 5,793,272 A | 8/1998 | Burghartz et al. .......... 336/200 |
| 5,843,139 A | 12/1998 | Goedeke et al. ............... 607/32 |
| 5,861,019 A | 1/1999 | Sun et al. ...................... 607/60 |
| 5,872,489 A | 2/1999 | Chang et al. ................ 331/179 |
| 5,884,990 A | 3/1999 | Burghartz et al. .......... 336/200 |
| 5,931,857 A | 8/1999 | Prieve et al. .................. 607/14 |
| 5,944,659 A | 8/1999 | Flach ......................... 600/300 |
| 6,014,586 A * | 1/2000 | Weinberg et al. ............. 607/36 |
| 6,026,325 A * | 2/2000 | Weinberg et al. ............. 607/36 |
| 6,054,329 A | 4/2000 | Burghartz et al. ............. 438/3 |
| 6,114,937 A | 9/2000 | Burghartz et al. .......... 336/200 |
| 6,567,703 B1 | 5/2003 | Thompson et al. ........... 607/60 |

\* cited by examiner

IMPLANTABLE MEDICAL DEVICE INCORPORATING MINIATURIZED CIRCUIT MODULE

This application is a of U.S. application Ser. No. 09/708,307, filed Nov. 8, 2000 now U.S. Pat. No. 6,567,703, now allowed.

FIELD OF THE INVENTION

This invention relates generally to implantable medical devices (IMDs) having RF telemetry capabilities for uplink transmitting patient data and downlink receiving programming commands to and from an external programmer, and more particularly to a miniaturized circuit module configured to occupy a small space within the IMD housing to further effect the miniaturization thereof.

BACKGROUND OF THE INVENTION

A wide variety of IMDs that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle and organ tissue stimulating medical devices are also known for treating a variety of conditions.

Currently available IMD IPGs including ICD and cardiac pacemaker IPGs are typically formed having a metallic housing that is hermetically sealed and, therefore, is impervious to body fluids, a header or connector assembly mounted to the housing for making electrical and mechanical connection with one or more leads, and possess telemetry capabilities for communicating with external devices. Over the past 20 years, ICD IPGs have evolved, as described in some detail in commonly assigned U.S. Pat. No. 5,265,588, from relatively bulky, crude, and short-lived ICD IPGs simply providing high energy defibrillation shocks to complex, long-lived, and miniaturized ICD IPGs providing a wide variety of pacing, cardioversion and defibrillation therapies. Numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. Moreover, the high voltage output circuitry has been improved in many respects to provide monophasic, biphasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

Such ICD IPGs need to be small enough to be comfortably implanted subcutaneously without being unduly uncomfortable to the patient or cosmetically apparent. The first implanted automatic implantable defibrillator (AID) IPG housing disclosed in U.S. Pat. No. 4,254,775 was very large and had to be implanted in a patient's abdominal region. Since that time, the ICD IPGs have been reduced in size while their complexity has been vastly increased. Battery energy requirements for powering both the low voltage integrated circuits (ICs) and for providing the cardioversion/defibrillation shocks have been reduced while battery energy density has been increased and battery configuration made more conforming to the interior space of the ICD IPG housing. Miniaturized, flat high voltage output capacitors that can be shaped to fit the allocated housing space and miniaturized high voltage switching components have been developed and employed. All of these improvements, together with the above-mentioned cardioversion/defibrillation improvements have contributed to a significant reduction in the volume of the ICD IPG housing without sacrificing longevity and capabilities.

Similar improvements in reducing housing volume have been made in other IMD IPGs, particularly implantable cardiac pacemakers, nerve stimulators and monitors, over the same time period. Remote programming and interrogation of IMD operating modes and parameters has been implemented in the above-described IMDs employing uplink (from the IMD) and downlink (to the IMD) telemetry transmissions between an RF transceiver within the IMD and an external transceiver of an external "programnmer". Such programmers are used to program the IMD by downlink telemetry transmission of commands that are received and stored in memory incorporated within the IMD that change an operating mode or parameter value governing a function performed by the IMD.

Both non-physiologic and physiologic data (collectively referred to herein as "patient data") can be transmitted by uplink RF telemetry from the IMD to the external programmer. The physiologic data typically includes stored and real time sampled physiologic signals, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies.

The RF telemetry transmission system that evolved into current common usage relies upon magnetic field coupling through the patient's skin of an ND IPG antenna with a closely spaced programmer antenna. Low amplitude magnetic fields are generated by current oscillating in an LC circuit of an RF telemetry antenna of the ND or programmer in a transmitting mode. The currents induced in the closely spaced RF telemetry antenna of the programmer or ND are detected and decoded in a receiving mode. Short duration bursts of the carrier frequency are transmitted in a variety of telemetry transmission formats. In the MEDTRONIC® product line, the RF carrier frequency is set at 175 kHz, and the IMD RF telemetry antenna located within the IMD housing is typically formed of coiled wire wound about a bulky ferrite core.

Apart from the bulk of the antenna taking up valuable space within the IMD housing, there are a number of other limitations in the current MEDTRONIC® telemetry system employing the 175 kHz carrier frequency. First, using a ferrite core, wire coil, RF telemetry antenna results in a very low radiation efficiency because of feed impedance mismatch and ohmic losses and a radiation intensity attenuated proportionally to at least the fourth power of distance (in contrast to other radiation systems which have radiation intensity attenuated proportionally to square of distance). These characteristics require that the implantable medical device be implanted just under the patient's skin and preferably oriented with the RF telemetry antenna closest to the patient's skin so that magnetic field coupling is provided. To ensure that the data transfer is reliable, it is necessary for the patient to remain still and for the medical professional to steadily hold the RF programmer head against the patient's skin over the IMD for the duration of the transmission. The time delays between downlink telemetry transmissions depend upon the user of the programmer, and there is a chance that the programmer head will not be held steady. If the uplink telemetry transmission link is interrupted by a gross movement, it is necessary to restart and repeat the uplink telemetry transmission.

Secondly, the RF telemetry data transmission rate is limited employing a 175 kHz carrier frequency. As device operating and monitoring capabilities multiply, it is desirable to be able to transmit out ever increasing volumes of data in real time or in as short a transmission time as possible with high reliability and immunity to spurious noise in an uplink telemetry transmission from an IMD, it is desirable to limit the current drain from the implanted battery as much as possible, simply to prolong IMD longevity.

As a result of these considerations, IMD-programnmer RF telemetry schemes have been proposed having the objectives of eliminating the bulky antenna within the IMD housing to conserve space, eliminating the need for the close, steady magnetic field coupling to enable uplink and downlink telemetry transmission at a greater distance, increasing the data transmission rate, and minimizing battery consumption. It has been proposed to replace the ferrite core, wire coil, RF telemetry antenna in the IMD with an antenna that can be located outside the hermetically sealed enclosure and to employ higher carrier frequencies and data transmission rates. It is suggested that the RF telemetry antenna may be located in the IPG header in U.S. Pat. No. 5,342,408. A further U.S. Pat. No. 4,681,111 suggests the use of a stub antenna associated with the header as the IMD RF telemetry antenna for high carrier frequencies of up to 200 MHz and employing phase shift keying (PSK) modulation. The elimination of the need for a VCO and a bit rate on the order of 2–5% of the carrier frequency or 3.3–10 times the conventional bit rate are alleged. In commonly assigned U.S. Pat. No. 5,861,019, it is proposed that the telemetry antenna be formed as a microstrip patch antenna that is conformal with the exterior housing of the IMD. The uses of the 204–216 MHz band and the 902–908 MHz ISM band have been proposed in U.S. Pat. Nos. 5,944,659 and 5,767,791 for telemetry transmissions between externally worn patient monitors and fixed location networked transceivers for ambulatory patient monitoring in a hospital context.

In order to fit within a minimal space, all electronic circuits of the IMD circuitry are preferably formed as ICs, but implementation of RF telemetry circuitry has required use of discrete capacitors and inductors mounted along with the RF IC to a circuit board. The use of such discrete inductors and capacitors is not eliminated, but is actually increased, in the above-described high frequency, high data transmission rate telemetry transceiver circuitry. The relocation of the bulky RF telemetry antenna to a less critical area outside the hermetically sealed IMD housing reduces space requirements. However, the discrete inductor and capacitor components mounted with one or more IC chip to an RF IC module substrate render the RF module unduly large such that it occupies a substantial portion of the volume within the IMD housing.

SUMMARY OF THE INVENTION

The present invention is directed to an IMD having a hermetically sealed chamber defined by a hermetically sealed housing, wherein the housing has an inner and an outer wall surface of a predetermined contour and enclosing a housing cavity or chamber of a predetermined volume. In accordance with a basic aspect of the present invention, the circuitry of the IMD comprises at least one circuit module comprising an IC chip mounted on a substrate and one or more discrete capacitor and/or micro-machined inductor that is/are selectively mounted directly or indirectly to the substrate in a manner reducing the volumetric form factor of the resulting circuit module.

In accordance with one embodiment of the invention, an RF module formed of an RF module substrate and at least one IC chip and discrete components has a volume and dimensions that are optimally minimized to reduce its volumetric form factor. In a first aspect of the invention, inductors are integrated into one or more IC chips mounted to the RF module substrate. In a further aspect of the invention, discrete capacitors are surface mounted over IC chips to reduce space taken up on the RF module substrate and to shorten the conductive paths between the IC and the capacitor. In a still further aspect of the invention, each IC chip is mounted into a well of the RF module substrate and short conductors are employed to electrically connect bond pads of the RF module substrate and the IC chip.

The inductors are preferably fabricated as planar spiral wound conductive traces formed of high conductive metals to reduce trace height and width while maintaining low resistance, thereby reducing parasitic capacitances between adjacent trace side walls and with a ground plane of the IC chip. The spiral winding preferably is square or rectangular, but having truncated turns to eliminate 90° angles that cause point-to-point parasitic capacitances.

The planar spiral wound conductive traces are further preferably suspended over the ground plane of the RF module substrate by micromachining underlying substrate material away to thereby reduce parasitic capacitances.

In these ways the form factor of the RF module is decreased, and the space within the IMD housing can be occupied by other components or can result in making the housing itself smaller and possibly thinner in profile than it would otherwise be. The form factor of other circuit modules of the IMD circuitry can also be reduced by employing the same techniques.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent to those skilled in the art from the following detailed description of a preferred embodiment, especially when considered in conjunction with the accompanying drawings in which.

DESCRIPTION OF THE PREFERRED EMBODIMENTS OF THE INVENTION

The present invention can be implemented in any IMD having high frequency RF telemetry capabilities. The present invention will be described in relation to a cardiac pacemaker or ICD IPG operating system design, but it is not intended that the invention be limited to that particular application when it can be advantageously implemented in various types of IMDs. At present, a wide variety of IMDs are commercially released or proposed for clinical implantation. Such medical devices include implantable cardiac pacemakers as well as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. As the technology advances, IMDs become ever more complex in possible programmable operating modes, menus of available operating parameters, and capabilities of monitoring increasing varieties of physiologic conditions and electrical signals which place ever increasing demands on the telemetry transmission system.

Figure 1:
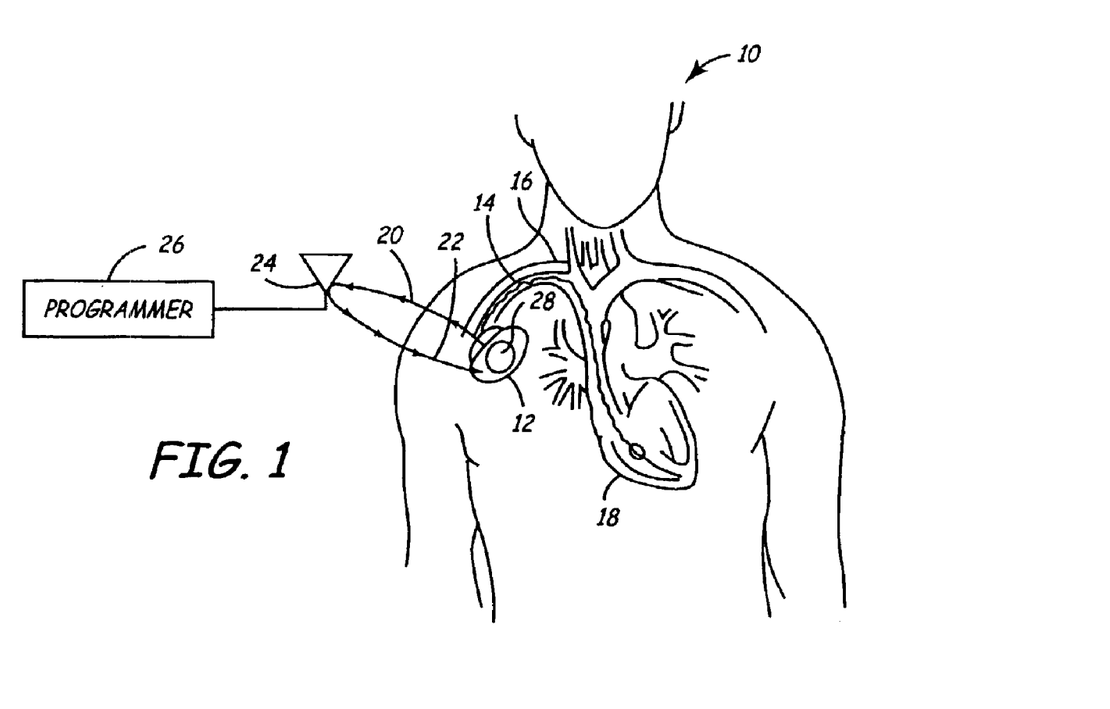
FIG. 1 is a simplified schematic view of an IMD constituting a cardiac pacemaker or ICD and an external programmer employing the improved RF telemetry antenna of the present invention.

FIG. 1 illustrates bi-directional telemetry communication between an external programmer 26 and an IMD, e.g., an ICD or cardiac pacemaker IPG 12, in accordance with the present invention. The IPG 12 is implanted in the patient 10 beneath the patient's skin or muscle and is typically oriented to the skin surface. The IPG 12 is electrically coupled to the heart 18 of the patient 10 through pace/sense or cardioversion/defibrillation electrodes and lead conductor(s) of at least one endocardial lead 14 coupled to the IPG connector in a manner known in the art. The IPG 12 contains a battery and an operating system powered by the battery that may employ a microcomputer or a digital state machine for timing and controlling device functions in accordance with a programmed operating mode. The operating system includes memory registers in RAM for storing a variety of programmed-in operating mode and parameter values that are used by the operating system. The memory registers may also be used for storing data compiled from sensed cardiac activity and/or relating to device operating history or sensed physiologic parameters for telemetry out on receipt of a retrieval or interrogation instruction.

When the IPG 12 is a cardiac pacemaker or is an ICD including pacing components, its operating system also includes sense amplifiers for detecting cardiac signals, pulse generating output circuits for delivering pacing pulses to at least one heart chamber of the heart 18, and optionally includes patient activity sensors or other physiologic sensors for sensing the need for cardiac output and modulating pacing parameters accordingly in a manner well known in the prior art. When the IPG 12 is an ICD, it includes one or more high power cardioversion/defibrillation output capacitor, electronic circuitry coupled to the sense amplifiers for detecting and discriminating pathologic and/or non-pathologic arrhythmias from one another and providing other functions, high voltage electronic charging circuitry for charging the output capacitor(s) from a battery voltage to a higher voltage, and electronic switching circuitry for dumping the charge built up on the output capacitor(s) through the cardioversion/defibrillation electrodes. Such a pacing or ICD IPG 12 is described in detail in commonly assigned U.S. Pat. No. 5,626,620 or 5,931,857, respectively.

The IPG operating system also includes telemetry circuitry and a telemetry antenna 28, which typically include relatively bulky discrete components described further below. The IPG telemetry antenna 28 can take the form of a surface mounted antenna described in the above-referenced '019 patent or an antenna enclosed within or mounted to the IPG connector. The physical space within the IPG housing is limited, and it is desirable to reduce the size of components fitting within it either to reduce the overall size and weight of the IPG 12 or to increase the battery size to increase longevity. In accordance with the present invention, the size of discrete components of the RF module of the IPG circuitry is decreased to accomplish that goal. By way of background to place this in context, the IPG telemetry system and functions are first described as follows.

Programming commands or data are transmitted between the IPG RF telemetry antenna 28 within or on a surface of the IPG 12 and an external RF telemetry antenna 24 associated with the external programmer 26. Preferably, a high frequency carrier signal in the range of 402 to 405 MHz is employed and it is not necessary that the external RF telemetry antenna 24 be contained in a programmer RF head so that it can be located close to the patient's skin overlying the IPG 12. Instead, the external RF telemetry antenna 24 can be located on the case of the external programmer some distance, e.g., about two to five meters, from the patient 10. For example, the external programmer 26 and external RF telemetry antenna 24 may be on a stand a few meters or so away from the patient 10 as described, for example, in the above-referenced '019 patent and in commonly assigned U.S. Pat. Nos. 5,683,432 and 5,843,139. Moreover, the patient 10 may be active and could be exercising on a treadmill or the like during an uplink telemetry interrogation of real time ECG or physiologic parameters. The programmer 26 may also be designed to universally program existing IPGs that employ the conventional ferrite core, wire coil, RF telemetry antenna of the prior art and therefore also have a conventional programmer RF head and associated software for selective use with such IPGs.

In an uplink telemetry transmission 20, the external RF telemetry antenna 24 operates as a telemetry receiver antenna, and the IPG RF telemetry antenna 28 operates as a telemetry transmitter antenna. Conversely, in a downlink telemetry transmission 22, the external RF telemetry antenna 24 operates as a telemetry transmitter antenna, and the IPG RF telemetry antenna 28 operates as a telemetry receiver antenna.

Figure 2:
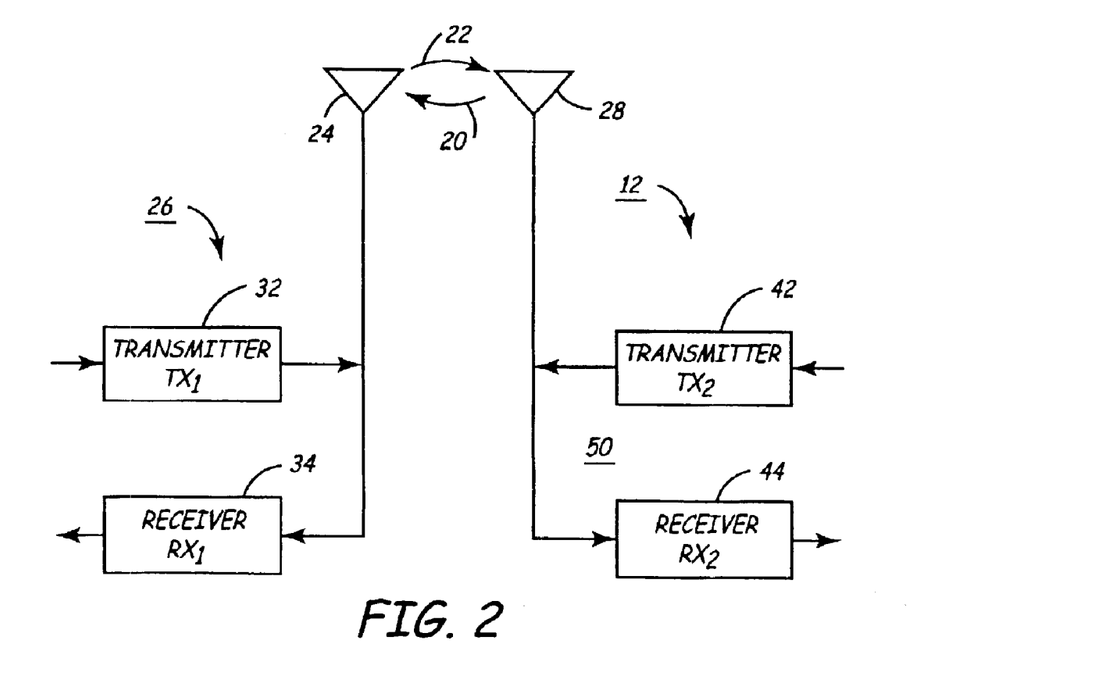
FIG. 2 is a simplified block diagram of major functional uplink and downlink telemetry transmission functions of the external programmer and IMD of FIG. 1.

FIG. 2 illustrates certain of the functional telemetry transmission blocks of the external programmer 26 and IPG 12 of FIG. 1. The external RF telemetry antenna 24 within the programmer 26 is coupled to a telemetry transceiver comprising a telemetry transmitter 32 and telemetry receiver 34. The programmer telemetry transmitter 32 and telemetry receiver 34 are coupled to control circuitry and registers operated under the control of a microcomputer and software as described in commonly assigned U.S. Pat. No. 5,843,139, for example. Similarly, within the IPG 12, the IPG RF telemetry antenna 28 is coupled to a telemetry transceiver comprising a telemetry transmitter 42 and telemetry receiver 44 incorporated into an RF module 50 that is further described below with reference to FIGS. 3 and 4.

In an uplink telemetry transmission 20, the telemetered data may be encoded in any of the telemetry formats. In a particular example described below, the data encoding or modulation is in the form of frequency shift key (FSK) modulation of the carrier frequency, for example. To initiate an uplink telemetry transmission 20, the telemetry transmitter 32 in external programmer 26 is enabled in response to a user initiated INTERROGATE command to generate an INTERROGATE command in a downlink telemetry transmission 22. The INTERROGATE command is received and demodulated in receiver 44 and applied to an input of the IMD central processing unit (CPU), e.g. a microcomputer (not shown). The IMD microcomputer responds by generating an appropriate uplink data signal that is applied to the transmitter 42 to generate the encoded uplink telemetry signal 20.

A simple bit stream format is employed that can be used to robustly transmit INTERROGATE commands or PROGRAM instructions under the control of a programmer CPU. Each RF pulse of the INTERROGATE instruction or command that is transmitted in the downlink telemetry transmission 22 causes the IPG antenna receiver 44 to ring. The train of induced voltages is detected and decoded by the receiver 44. After the INTERROGATE command or instruction is decoded, the stored data to be uplink transmitted is encoded into PPM modulated RF pulses in data frames, for example. The IPG transmitter 42 applies voltage to the IPG RF antenna 28 to generate the uplink RF pulses which are transmitted through the patient's body and the intervening air to the external RF telemetry antenna 24. The transmitted signals are detected in the telemetry receiver 34 and applied as a pulse train to further decoding circuitry to decode the transmitted data so that at the data can be recorded or displayed as described above.

The uplink and downlink telemetry transmissions follow a telemetry protocol that formulates, transmits and demodulates data packets each comprising a bit stream of FSK modulated data bits. A carrier frequency centered in a 300 kHz band between 402 MHz and 405 MHz is modulated in frequency or frequency shifted up representing a data bit "1" or "0" or shifted down to represent the other data bit. The data packets are formulated of an FSK data bit stream with a preamble, data and error checking data bits.

Figure 3:
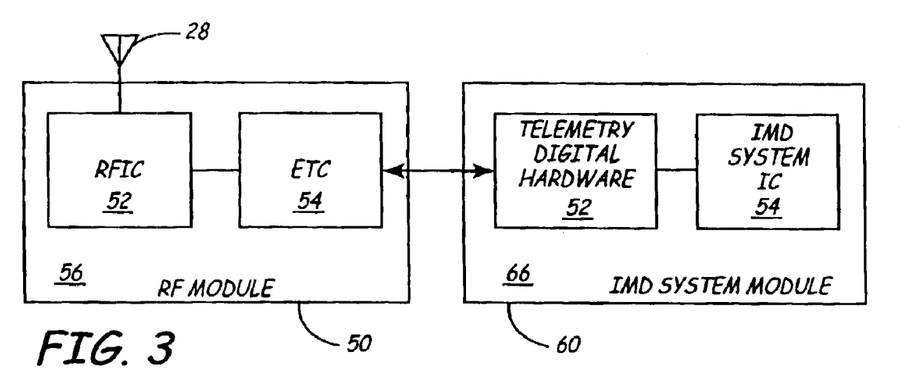
FIG. 3 is a simplified block diagram of the transceiver components of the IMD of is FIG. 1.

FIG. 3 further schematically depicts the IPG telemetry circuitry which is embodied in the RF module 50 and the IMD system module 60. The RF telemetry module 50 is physically embodied in a miniaturized circuit board 56 on which are mounted the RF IC chip 52, the electronic control (ETC) chip 54, a number of discrete components described further below, bonding pads and conductors formed on the surface of the circuit board 56. Electrical connections are made between certain of the bonding pads and the IMD system module 60 or a feedthrough pin (not shown) extending through the IPG housing wall (not shown) and coupled to the IPG RF antenna 28. The IMD system module 60 similarly is embodied in a miniaturized circuit board 66 on which are mounted at least one IMD system chip 62, telemetry digital hardware interface 64, a number of discrete components, and deposited bonding pads and conductors for making electrical connections therebetween and with further components of the IMD which play no role in the present invention. The printed circuit boards or substrates 56 and 66 are formed in the typical manners of epoxy-glass and polyamide flex printed wiring boards, ceramic or silicon substrates including employing silicon wafer scale integration techniques.

The hardware interface 64 comprises uplink and downlink RAM buffers, control and status registers, and interrupt lines as well as a synchronous serial bus, transmit and receive serial data lines, a frequency standard input to the phase detector and AFC control lines. The hardware interface 64 includes a baseband receiver signal processor, a protocol physical layer controller, a CPU, and RAM and functions as the RF module controller and interface. In the receive mode, the baseband receiver signal processor implements an AFC frequency control of the VCO and provides bit synchronization and demodulation functions from the received data bit stream of each packet so that the received data is demodulated without errors. The protocol physical layer controller functions to detect the preamble of the packet and to perform CRC processing of the CRC data bits of the packet for both the transmit and receive operations.

Figure 4:
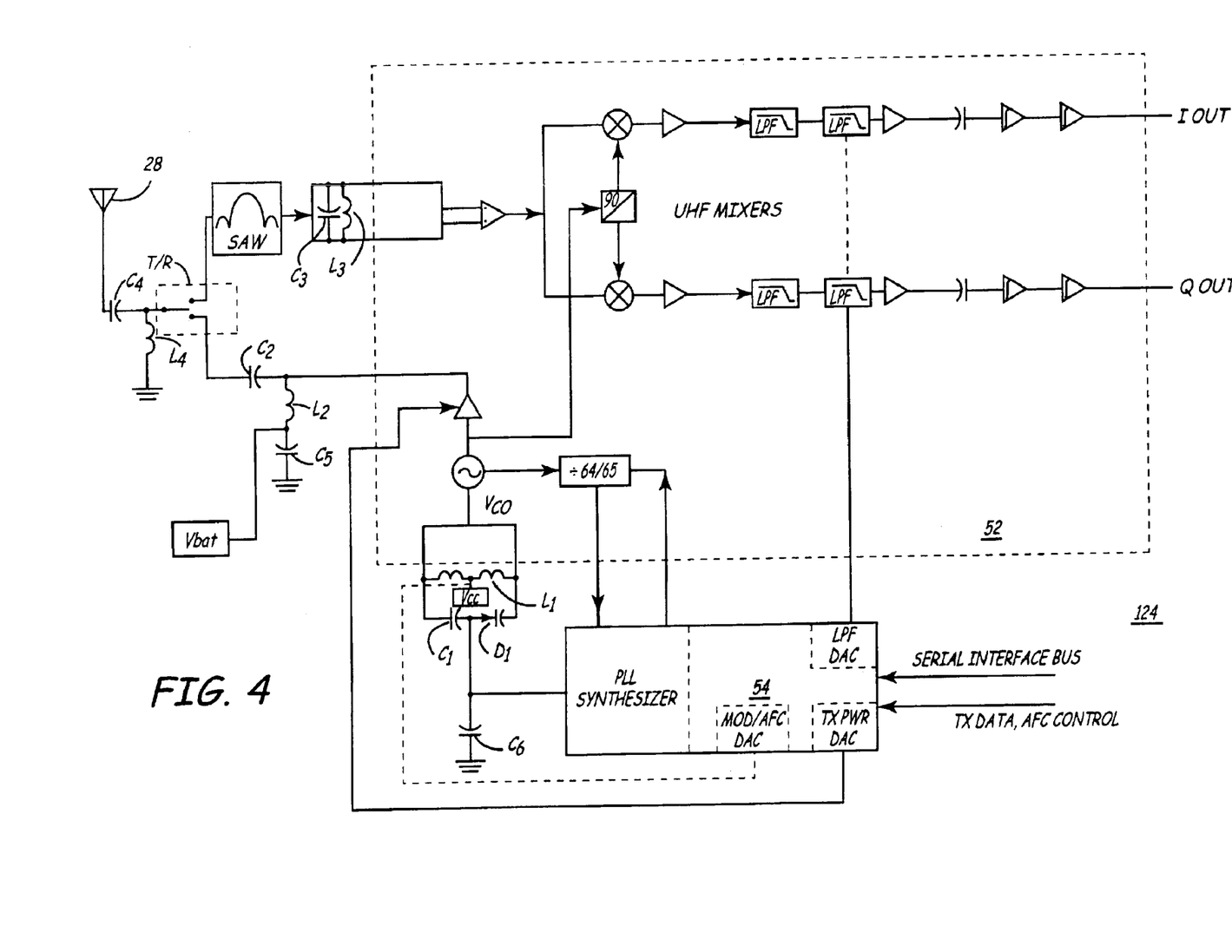
FIG. 4 is a schematic circuit of the RF module of FIG. 3.

FIG. 4 depicts the circuitry of the RF module 50 including the RF IC chip 52, the ETC chip 54 and the discrete components that provide the functions of a "Zero IF" receiver 44, an FSK transmitter 42, a UHF Frequency Synthesizer providing both local oscillator injection to the UHF receiver's UHF Mixers, and a Frequency Shift Key (FSK) FM carrier for the FSK transmitter 42. In a" downlink telemetry receive mode, INPHASE (I) and QUADRATURE (Q) baseband IF signals are developed by the RF Mixers in the RF IC chip 52 that are forwarded for digital demodulation and bit sync and signal processing by the telemetry digital hardware 64. In an FSK uplink telemetry transmit mode, TX DATA is encoded in ETC chip 54 and uplink telemetered by FSK modulation of the carrier signal developed by a voltage controlled oscillator (VCO) resident in part on the RF IC chip 52 and in a tank circuit formed of discrete inductor L1, capacitor C1 and diode D1.

The ETC chip 54 is a mixed signal chip that provides a phase detector, charge pump, lock detector and programmable counters of the frequency synthesizer, an FSK modulator, an AFC control, current DACs for setup of the RF IC chip 52, and a controller interface. The discrete components of the RF module 50 include the phase lock loop (PLL) loop filter capacitor C1, inductor L1, tuning varactor diode D1, a surface acoustic wave resonator SAW, and an antenna transmit/receive switch T/R. In addition, further discrete inductors L2, L3, L4 and capacitors C2, C3, C4, C5, C6 are required for proper circuit functions coupled to the antenna 28 directly or through the transmit/receive switch T/R or to the SAW. Additionally, mutually coupled inductors, in the form of transformers, can be used as baluns to drive balanced circuits and also to provide direct and broadband impedance transformations. The transformer function could be used for driving diode bridges in balanced mixers and impedance matching from 50 ohm unbalanced impedances (i.e., antennas) to the higher, balanced, impedances present in low current RF ICs.

Figure 5A:
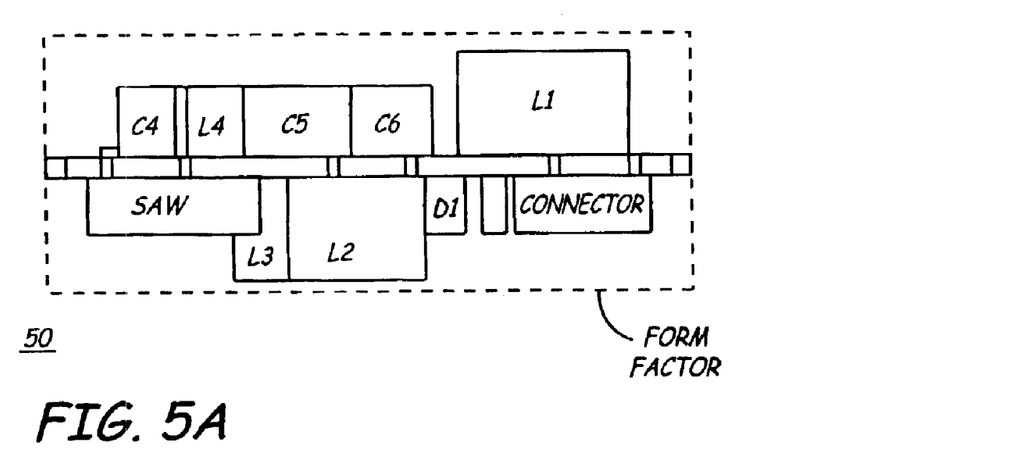
FIGS. 5A and 5B are side and bottom views, respectively of the physical layout and size of the RF module of FIGS. 3 and 4 employing conventional discrete inductors and capacitors defining a volumetric form factor.
Figure 5B:
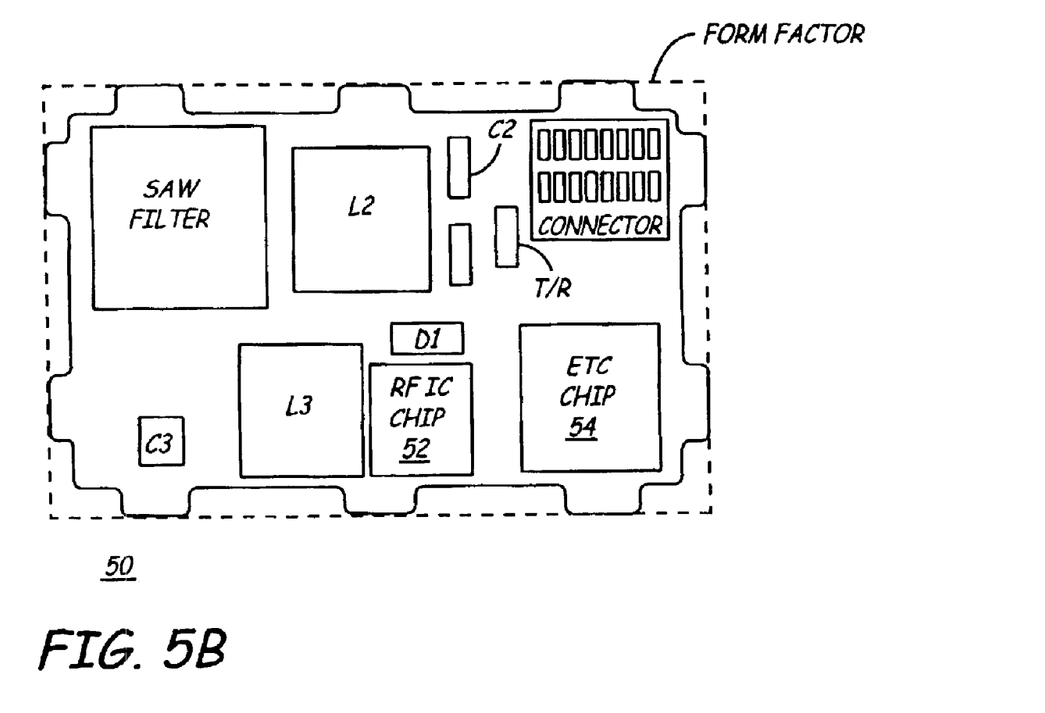

In the prior art, these discrete components L1–L4 and C1–C6 would be electrically mounted on the RF module substrate 56 and connected to pads of the RF IC 52 or the ETC IC 54 or to other discrete components mounted to the RF module substrate 56 as shown, for example, in FIGS. 5A and 5B. The small value discrete inductors L1–L5 (from 5 to 45 nanoHenries) must have very high quality factors (or Q) that are greater than or equal to 60 at the carrier frequency $f_c$ and L values. These requirements have dictated the use of discrete wire wound, air core inductors that have the requisite inductance and Q and that are bonded to bonding pads of the RF module substrate 56.

Similarly, the small value capacitors (from 0.5 to 39 pF) must have Qs in excess of 150 at the carrier frequency $f_c$. Chip capacitors raise inductance issues with present interconnect methods (i.e., substrate traces, and wire bonds). Typically, the capacitor values are chosen to series resonate with the wirebond/trace inductance. This often requires multiple capacitors for effectively providing broadband bypassing to ground. If the inductance is minimized, the self-resonant frequency of the capacitor can be raised high enough to minimize this effect.

It is conventional practice to mount discrete capacitors to bonding pads on the surface of the RF module substrate 56. But, such mounting requires substrate conductors extending from the bonding pads to bonding pads adapted to be electrically connected to IC bonding pads by conductors that bridge the physical gap. Parasitic capacitances develop between such substrate conductors and bridging conductors and adjacent conductors and the substrate ground plane that must be compensated for.

Moreover, the provision of the bonding pads and conductive traces from the bonding pads to other bonding pads on a surface of the RF module substrate 56 increases the overall length and width of the RF module substrate 56 to provide the surface real estate. The discrete capacitors and inductors are typically packaged in a hexahedral form having a package length and width defining the surface mount area and a height extending from a surface mounting or floor side and the free or roof side. The three-dimensions and the resulting hexahedral envelope volume is referred to as a "form factor" of the RF module 50. The RF module form factor is therefore dictated by the number, sizes and required spacing of these discrete inductors and capacitors, other discrete components described above, the RF IC chip 52 and ETC IC chip 54, edge bonding pads for connection with IMD system module 60 and the battery, and the conductors or conductive traces electrically connecting them together.

FIGS. 5A and 5B depict such a three dimensional RF module 50 having a plurality of discrete inductors, capacitors and ICs mounted to and projecting from the top and bottom surfaces of the RF module substrate 56 following conventional surface mount fabrication processes that are modified following the teachings of the present invention. The inductors L1–L5 project outward the furthest from the top and bottom surfaces of RF module substrate 56 and thereby define the overall thickness of the form factor 61 defining the spatial volume occupied within the IMD housing sealed chamber. Moreover, the locations of the inductors L1–L5 against the top and bottom surfaces of RF module substrate 56 spaced away from the RF IC chip 52 and the ETC chip 54 consume surface area or "real estate" of the top and bottom surfaces of RF module substrate 56, thereby is increasing its overall length and width and the corresponding length and width dimensions of the hexahedral form factor 61.

Similarly, the discrete capacitors C1–C6 are surface mounted and coupled to bonding pads on the top and bottom surfaces of RF module substrate 56 spaced away from the RF IC chip 52 and the ETC chip 54. These substrate surface mounts also consume real estate of the top and bottom surfaces of RF module substrate 56, thereby increasing its overall length and width and the corresponding length and width dimensions of the hexahedral form factor 61.

Additionally, the RF IC chip 52 and ETC chip 54 are surface mounted and coupled to bonding pads on the top and bottom surfaces of RF module substrate 56 spaced away from the RF IC chip 52 and the ETC chip 54. The substrate surface mounting of the IC chips cause the IC chips to project outward and lengthens the conductors extending between exposed surface IC chip bonding pads and bonding pads on the RF module substrate 56. Such elevated and lengthened conductors increase parasitic capacitances and inductances.

Figure 6A:
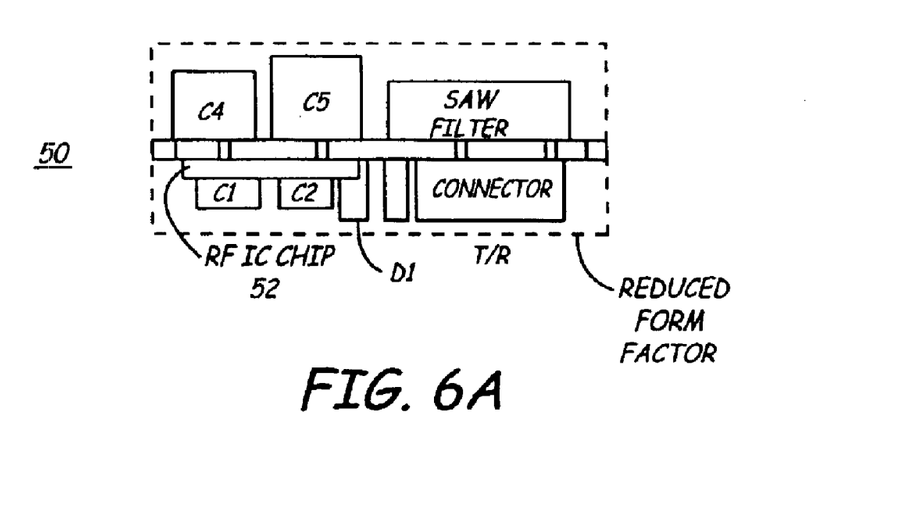
FIGS. 6A and 6B are side and bottom views, respectively of the physical layout and size of the RF module of FIGS. 3 and 4 employing IC fabricated inductors, IC mounted capacitors and particular IC mounting techniques of the present invention defining a reduced sized volumetric form factor.
Figure 6B:
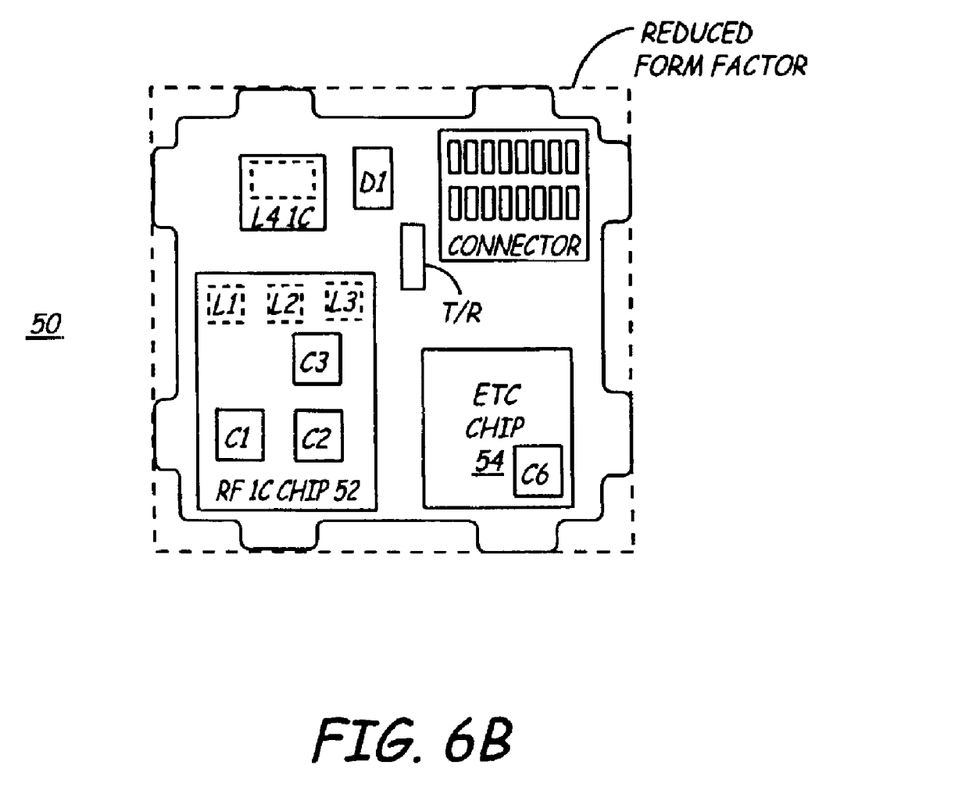

The present invention involves integration of the inductors into the RF IC chip 52 and/or the ETC chip 54 to effectively eliminate the discrete inductors and thereby reduce the height and volume of the RF module as shown in the three dimensional RF module 50 depicted in FIGS. 6A–6B. In this illustrated example, the inductors L1–L3 are incorporated into RF IC chip 52, and capacitors C1–C3 are mounted to RF IC chip 52. Capacitor C6 is mounted to ETC chip 54, and a discrete IC is provided for inductor L4 to provide for ready connection with the T/R switch. Alternatively, at least inductor L1 and capacitor C1 could be incorporated into or mounted onto ETC chip 54.

According to conventional practice in IMD design and fabrication, inductors are not presently integratable into an IC due to a high value of parasitic capacitance to the substrate as $Q_p = Rp/(2*PI*f*L)$ where Rp (parallel resistance) is due to intrinsic substrate conductivity. Another limiting factor in inductor Q is Rs or series resistance as $Q_s = (2*PI*f*L)/Rs$. Series resistance, in this case, is primarily due to effective conductivity of the inductor's conductor (with skin effect and surface roughness effects is included). Both effects must be included in determining the actual Q for the inductance ($Q_{actual} = 1/((1/Q_s) + (1/Q_p))$).

Figure 7:
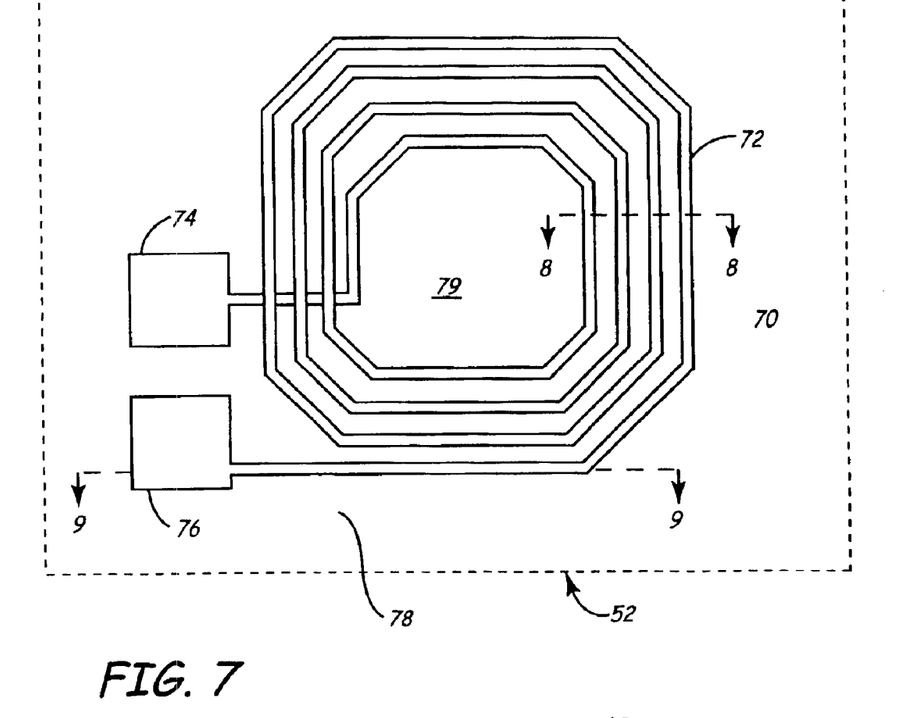
FIG. 7 is a schematic illustration of a spiral wound inductor formed by IC fabrication processes on the RF IC.

However, it is feasible to fabricate certain of the high Q inductors by integration of inductors onto the surface of an ASIC IC, e.g., RF IC 52 and/or ETC IC 54, if certain design features and fabrication techniques are employed. Referring to FIG. 7, first, the design of the inductor 70 is in the shape of a planar spiral 72 formed on IC surface 78 extending between bonding pads 74 and 76 coupled to first and second ends of the planar spiral 72. The first end of the planar spiral 72 is coupled through a via to a conductive trace disposed below the IC surface 78 and extending laterally across the planar spiral 72 and is in turn coupled to the bonding pad 74 by way or a further via. These fabrication techniques are described, for example, in "RF Circuit design Aspects of Spiral Inductors on Silicon", Burghartz, et al., *IEEE Journal of Solid-State Circuits*, Vol 33, No. 12, December, 1998, pp. 2028–34 and in U.S. Pat. Nos. 5,793,272, 5,884,990, 6,054,329, 6,114,937, and 5,416,356.

The spiral turns of planar spiral 72 are arranged around an open central area 79 because tightly wound centrally disposed spirally wound central turns add significant resistance R without contributing any appreciable inductance L. Furthermore, the planar spiral 72 is implemented with diagonal corners to minimize impedance mismatch (and thus energy losses) of a right angle design.

Figure 8:
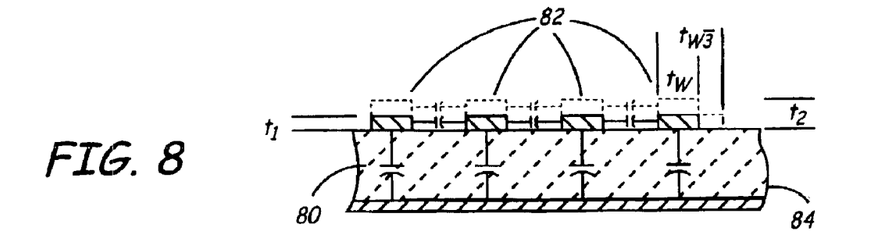
FIG. 8 is a partial cross-section view taken along lines 8—8 of FIG. 7 illustrating fabrication of the traces forming the spiral turns of the spiral inductor of FIG. 7.

The spiral turns are deposited as a continuous trace 82 on IC surface 78 or as a layer of IC substrate 80 preferably using a high conductivity conductor selected from the group consisting of gold, copper or aluminum-copper metallization instead of standard aluminum or aluminum silicide metallization. Copper has less than one-half the impedance of similar thickness aluminum. Therefore the thickness or wall height of the traces can be reduced as shown in FIG. 8 from the dotted line thickness $t_2$ to the solid line thickness $t_1$. The reduction in thickness or trace wall height using copper metallization also reduces wall-to-wall parasitic capacitance by one-half. Moreover, parasitic capacitance across IC substrate 80 to an underlying conductive ground plane 84 may be reduced 30% because the track width $t_w$ may be reduced to 70% of an equivalent aluminum track width $t_{wa}$ at the same impedance level.

Figure 9:
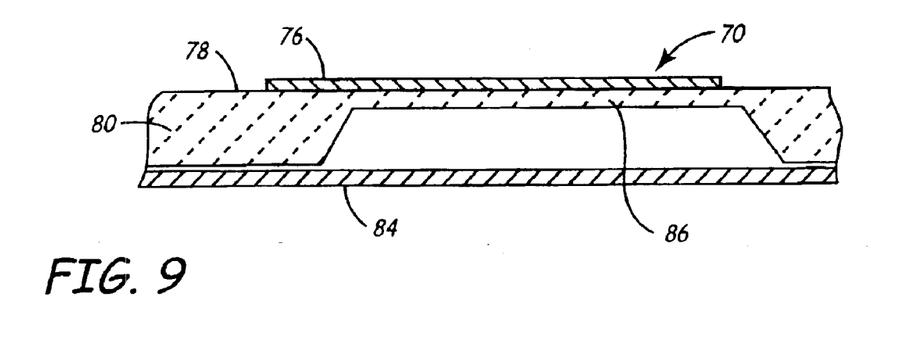
FIG. 9 is a partial cross-section view taken along lines 9—9 of FIG. 7 illustrating fabrication of the traces forming the spiral turns of the spiral inductor of FIG. 7 suspended on a platform.

Substrate capacitance of the inductor is additionally substantially reduced by the implementation of the spiral inductor 70 on a micromachined (MEM) platform 86 as shown in FIG. 9. Additionally, a SOI substrate should optimally be used. A segmented ground plane 84 may optionally be added. The SOI substrate 80 is etched to a thin platform 86 by back etching as is known in the art and described, for example, in "Suspended SOI Structure for Advanced 0.1 μm CMOS RF Devices", Hisamoto, et al., *IEEE Transactions on Electron Devices*, Vol 45, No. 5, May 1998, pp. 1039–46. Leaving the thin platform 86 in place rather than fully etching the silicon substrate away makes the planar spiral 72 more readily producible and robust. However, it will be understood that the planar spiral 72 could be fully suspended without a planar support.

Figure 10:
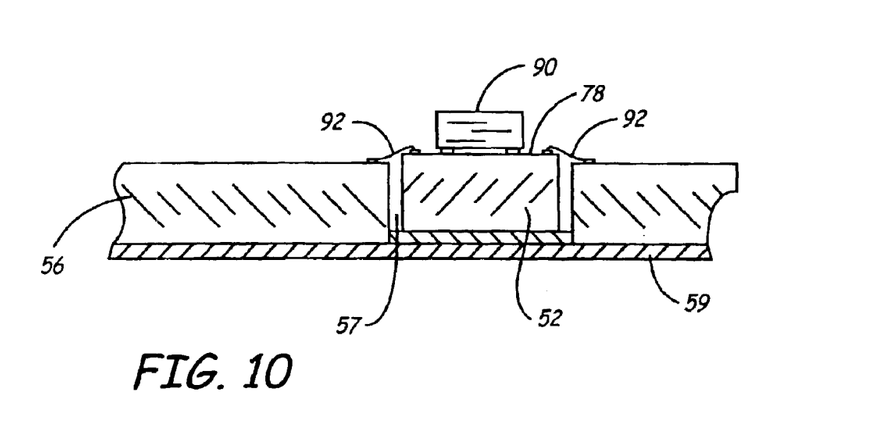
FIG. 10 is a side view in partial cross-section showing the mounting of the RF IC in a well of the RF module substrate and a discrete capacitor surface mounted to the RF IC surface.

Additionally, chip inductor and capacitor integration may be accomplished by using "wafer scale integration" techniques whereby capacitor (or inductor) contact areas are integrated onto the surface of a RF IC 52. FIG. 10 shows that the RF IC 52 is placed in a well 88 of the RF module substrate 56, and that a discrete capacitor 90 is fitted over it. The small chip capacitor 90 (such as 68 pF 0.01×0.01" Dielectric Labs, Inc., Part No. D10) can be soldered or epoxy attached directly to the surface 78 of the RF IC 52. This direct IC mounting eliminates substantial parasitic high frequency impedance, capacitance and/or inductance caused by IC routing to the edge of the die, wire bonds to the supporting substrate, substrate interconnect to substrate pads and substrate pads and allows the capacitors to be reduced in size. The capacitor body may be placed over active IC functional circuitry to further reduce die area. Additionally the RF IC 52 may be placed in a well 57 within RF module substrate 56 over substrate ground plane 59 to minimize the length of wire bond wires 92 and thereby reducing parasitic capacitance and inductance occasioned by longer wires required when the RF IC 52 is surface mounted to substrate 56.

Utilizing these fabrication techniques advantageously reduces the form factor (i.e., size, volume) of all the circuitry of the RF module 50, minimizes substrate noise and/or coupling, improves performance, reduces fully allocated product costs (FAPC), and does not introduce any substantial packaging issues. Standard wafer fabrication processes can also be economically employed. Further articles relating to fabrication processes that can be employed include: "Micromachined Planar Spiral Inductor in Standard GaAs HEMT MMIC Technology", Ribas, et al., *IEEE Electron Device Letters*, Vol. 19, No. 8, August 1998, pp. 285–7; "Analysis, Design, and Optimization of Spiral Inductors and Transformers for Si RF IC's", Niknejad, et al., *IEEE Journal of Solid-State Circuits*, Vol 33, No. 10, October 1998, pp. 1470–81; "A Novel High-Q and Wide-Frequency-Range Inductor Using Si 3-D MMIC Technology", Kamogawa, et al., *IEEE Microwave and Guided Wave Letters*, Vol 9, No. 1, January 1999, pp. 16–18; "Integrated Circuit Technology Options for RFIC's—Present Status and Future Directions", Larson, *IEEE Journal of Solid-State Circuits*, Vol 33, No. 3, March 1998, pp. 387–99; and "Micromachined Electro-Mechanically Tunable Capacitors and Their Applications to RF IC's", Dec et al., *IEEE Transactions on Microwave Theory and Techniques*, Vol 46, No. 12, December 1998, pp. 2587–95.

All patents and other publications identified above are incorporated herein by reference.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. An implantable medical device operable to perform a therapeutic and/or monitoring function comprising:

a housing having a housing side wall and inner and outer wall surfaces of a predetermined contour enclosing a hermetically sealed chamber;

a battery enclosed within said hermetically sealed chamber; and an electronic module powered by said battery having a volumetric form factor dimensioned to fit within said hermetically sealed chamber along with said battery, said electronic module comprising a module substrate board, a plurality of discrete components and at least one integrated circuit IC chip;

said module substrate having a predetermined module substrate thickness with a well formed in said module substrate extending from a module substrate surface through at least a portion of said module substrate thickness, and at least one module bonding pad formed on the electronic module substrate surface, said IC chip having a predetermined IC chip substrate thickness, at least one IC bonding pad formed on an exposed IC chip surface, and said IC chip mounted within said well of said electronic module substrate thereby reducing the form factor of the electronic module, and a conductor extending between said module bonding pad and said IC bonding pad.

2. The implantable medical device of claim 1, wherein said electronic module further comprises an RF module incorporating a telemetry transceiver.

3. The implantable medical device of claim 2, further comprising at least one discrete capacitor mounted to said exposed IC chip surface.

4. The implantable medical device of claim 2, further comprising at least one IC inductor formed integrally with the IC chip substrate thereby reducing the form factor of the RF module.

5. The implantable medical device of claim 4, further comprising at least one discrete capacitor mounted to said exposed IC chip surface.

6. The implantable medical device of claim 1, further comprising at least one IC inductor formed integrally with the IC chip substrate thereby reducing the form factor of the electronic module.

7. An implantable medical device operable to perform a therapeutic and/or monitoring function comprising:

a housing having a housing side wall and inner and outer wall surfaces of a predetermined contour enclosing a hermetically seated chamber;

a battery enclosed within said hermetically sealed chamber; and an electronic module powered by said battery having a volumetric form factor dimensioned to fit within said hermetically sealed chamber along with said battery, said electronic module comprising a module substrate board, and at least one discrete component and at least one integrated circuit IC chip are mounted to said electronic module, and wherein at least one discrete capacitor is mounted to said exposed IC chip surface thereby reducing the form factor of the electronic module, said IC chip has at least IC bonding pad formed on an exposed IC chip surface, and said at least one discrete capacitor is electrically connected to said at least one IC bonding pad.

8. The implantable medical device of claim 7, wherein said electronic module further comprises an RF module incorporating a telemetry transceiver.

9. The implantable medical device of claim 8, further comprising at least one IC inductor formed integrally with the IC chip substrate thereby reducing the form factor of the RF module.

10. The implantable medical device of claim 7, further comprising at least one IC inductor formed integrally with the IC chip substrate thereby reducing the form factor of the electronic module.

* * * * *

UNITED STATES PATENT AND TRADEMARK OFFICE
CERTIFICATE OF CORRECTION

PATENT NO. : 6,889,084 B2
DATED : May 10, 2005
INVENTOR(S) : Eiji Inoue et al.

It is certified that error appears in the above-identified patent and that said Letters Patent is hereby corrected as shown below:

Column 17,
Line 14, "stat;" should read -- state; --.

Column 18,
Line 1, "aids" should read -- side --.
Line 15, "reaped" should read -- respect --.
Line 26, "purse" should read -- pulse --.

Column 19,
Line 21, "tile" should read -- the --.

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,889,084 B2  
APPLICATION NO. : 10/403742  
DATED : May 3, 2005  
INVENTOR(S) : Gregory J. Haubrich et al.

It is certified that error appears in the above-identified patent and that said Letters Patent is hereby corrected as shown below:

Col. 13, line 16, please delete "hermetically seated" and insert --hermetically sealed--.

Signed and Sealed this

Second Day of January, 2007

JON W. DUDAS  
*Director of the United States Patent and Trademark Office*